(12) United States Patent
Gross (10) Patent No.: US 7,416,562 B2
(45) Date of Patent: Aug. 26, 2008

(54) TENSIONING INTRAOCULAR LENS ASSEMBLY

(76) Inventor: Yosef Gross, 10 HaNotea Street, Moshav Mazor 73160 (IL)

( * ) Notice: Subject to any disclaimer, the term of this patent is extended or adjusted under 35 U.S.C. 154(b) by 237 days.

(21) Appl. No.: 10/522,199

(22) PCT Filed: Jul. 29, 2003

(86) PCT No.: PCT/IL03/00626

§ 371 (c)(1),
(2), (4) Date: Jan. 24, 2005

(87) PCT Pub. No.: WO2004/010904

PCT Pub. Date: Feb. 5, 2004

(65) Prior Publication Data

US 2005/0251253 A1    Nov. 10, 2005

(51) Int. Cl.
*A61F 2/16* (2006.01)
(52) U.S. Cl. ...................... 623/6.13; 623/6.37

(58) Field of Classification Search ............... 623/6.13, 623/6.14, 6.22, 6.37–6.43
See application file for complete search history.

(56) References Cited

U.S. PATENT DOCUMENTS

| | | | | |
|---|---|---|---|---|
| 4,466,705 A | * | 8/1984 | Michelson | 623/5.16 |
| 4,713,072 A | * | 12/1987 | Bowald | 623/6.13 |
| 4,888,012 A | | 12/1989 | Horn et al. | |
| 5,476,514 A | | 12/1995 | Cumming | |
| 2002/0188351 A1 | * | 12/2002 | Laguette | 623/6.24 |

FOREIGN PATENT DOCUMENTS

EP    0356050    2/1990

* cited by examiner

*Primary Examiner*—William H. Matthews
(74) *Attorney, Agent, or Firm*—Dekel Patent Ltd.; David Klein (57) ABSTRACT

An intraocular lens assembly (70) including a lens assembly comprising an interface element adapted for attachment to an ocular structure, the lens assembly comprising a tensing element (76) adapted to expand and contract relative to the lens assembly and apply a tensing force on the ocular structure directed towards an inner volume of the lens assembly.

8 Claims, 7 Drawing Sheets

TENSIONING INTRAOCULAR LENS ASSEMBLY

FIELD OF THE INVENTION

The present invention relates generally to intraocular lens (IOL) assemblies and particularly to accommodating IOL assemblies.

BACKGROUND OF THE INVENTION

Natural accommodation in a normal human eye having a normal human crystalline lens involves automatic contraction or constriction and relaxation of the ciliary muscle of the eye (and zonules controlled by the ciliary muscle) by the brain in response to looking at objects at different distances. Ciliary muscle relaxation, which is the normal state of the muscle, shapes the human crystalline lens for distant vision. Ciliary muscle contraction shapes the human crystalline lens for near vision. The brain-induced change from distant vision to near vision is referred to as accommodation.

Accommodating intraocular lens (IOL) assemblies have been developed that comprise an IOL that moves in response to ciliary muscular contraction and relaxation, thereby to simulate the movement of the natural lens in the eye, and, inter alia, help provide patients with better focusing ability.

One example of an accommodating IOL assembly is described in U.S. Pat. No. 5,476,514 to Cumming. Cumming describes an accommodating IOL with plate haptics for implantation within the capsular bag of the eye, after removal of the natural lens by an anterior capsulotomy. During a postoperative healing period following surgery, anterior capsular remnants fuse to the posterior capsule of the bag by fibrosis about the plate haptics, and the lens is deflected rearward to a distant vision position against the elastic posterior capsule of the bag in which the posterior capsule is stretched rearward. After fibrosis is complete, natural brain-induced contraction and relaxation of the ciliary muscle relaxes and stretches the fused remnants and increases and reduces vitreous pressure in the eye, respectively, to effect vision accommodation by the fused remnants, the posterior capsule, and vitreous pressure.

However, prior art accommodating IOLs have certain drawbacks. For example, they do not address the problem of loss of accommodation in the eye. Accommodation may be lost during the aging process due to hardening of the natural lens. Loss of accommodation due to a progressive denaturation of the lens proteins produces an abnormal condition commonly known as "presbyopia". Presbyopia generally affects individuals in the early to mid forties and the resultant gradual loss of visual acuity is generally treated with bifocal spectacles.

Accommodation may also be lost due to a change in the size of the lens, with a resultant loss in tension of the zonules, thereby affecting the ability of the zonules to focus the lens. This loss in accommodation may occur with aging, but may also occur upon removal of the natural lens. For example, in a normal human eye, the diameter of the crystalline lens may be approximately 8-9.5 mm, and may have an anterior-posterior thickness of approximately 4.5 mm. After removal of the cortex and nucleus of the lens, such as after phacoemulsification in cataract surgery, the capsular bag may extend to 10.5 mm and have a width of only 2.0 mm. This causes a slackening of the zonules, which is not restored by prior art apparatus or methods upon insertion of an IOL. Thus an IOL assembly that retains the accommodation ability of the eye, including the ability of the zonules to focus the lens, is greatly needed.

SUMMARY OF THE INVENTION

The present invention seeks to provide an improved accommodating IOL assembly, which, inter alia, provides tensing of the zonules.

In the prior art, haptics generally exert an outwardly directed force to the capsular bag (and consequently to the zonules) in order to fix the IOL in the posterior chamber or some portion of the capsular bag. In contrast to the prior art, in the present invention, the lens assembly does not apply an outwardly directed force, rather an inwardly directed force that tenses the zonules. The tensing force tends to restore the natural accommodation capability of the eye, and enables the zonules to control the optical power of the lens as in the normal operation of a young, healthy eye. The present invention thus provides a lens assembly adapted for attachment to an ocular structure, and adapted to selectively tense and pull the ocular structure in a controlled manner.

There is thus provided in accordance with an embodiment of the present invention an intraocular lens (IOL) assembly comprising a lens assembly comprising an interface element adapted for attachment to an ocular structure, the lens assembly comprising a tensing element adapted to expand and contract relative to the lens assembly and apply a tensing force on the ocular structure directed towards an inner volume of the lens assembly.

In accordance with an embodiment of the present invention the tensing element comprises a selectively inflatable and deflatable member, the selectively inflatable and deflatable member being inflatable with a fluid.

Further in accordance with an embodiment of the present invention the selectively inflatable and deflatable member comprises at least one at least partially annular channel formed in the inner volume of the lens assembly. The at least one at least partially annular channel may be generally concentric with a central axis of the lens assembly.

In accordance with an embodiment of the present invention the selectively inflatable and deflatable member is formed with apertures through which the fluid flows.

Further in accordance with an embodiment of the present invention the selectively inflatable and deflatable member is adapted to absorb and expel the fluid by osmotic pressure.

Still further in accordance with an embodiment of the present invention the selectively inflatable and deflatable member comprises a biodegradable plug adapted to degrade with time. The interface element may comprise at least one of a roughened surface, a protrusion, a haptic, growth factor and biological adhesive.

In accordance with an embodiment of the present invention the tensing element comprises a variably expansive member that extends from one portion of the lens assembly to another portion of the lens assembly, wherein in a first configuration the variably expansive member is not adapted to apply a tensing force on the ocular structure, and in a second configuration the variably expansive member is adapted to apply a tensing force on the ocular structure.

Further in accordance with an embodiment of the present invention in the first configuration, the variably expansive member applies a preload to the lens assembly that pushes the perimeter of the lens assembly towards ocular structure.

Still further in accordance with an embodiment of the present invention the selectively inflatable and deflatable member comprises at least one inflatable and deflatable haptic.

In accordance with an embodiment of the present invention the at least one inflatable and deflatable haptic comprises an annular segment attached to the selectively inflatable and deflatable member by means of a strut. The spaces between anterior and posterior faces of the selectively inflatable and deflatable member and the lens assembly may be filled with a fluid.

Further in accordance with an embodiment of the present invention the lens assembly comprises at least one of a monofocal lens, multi-focal lens, a lens having a graded index of refraction, a holographic lens, a doublet lens, a Fresnel lens, a diffracting lens, and a telescopic lens.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
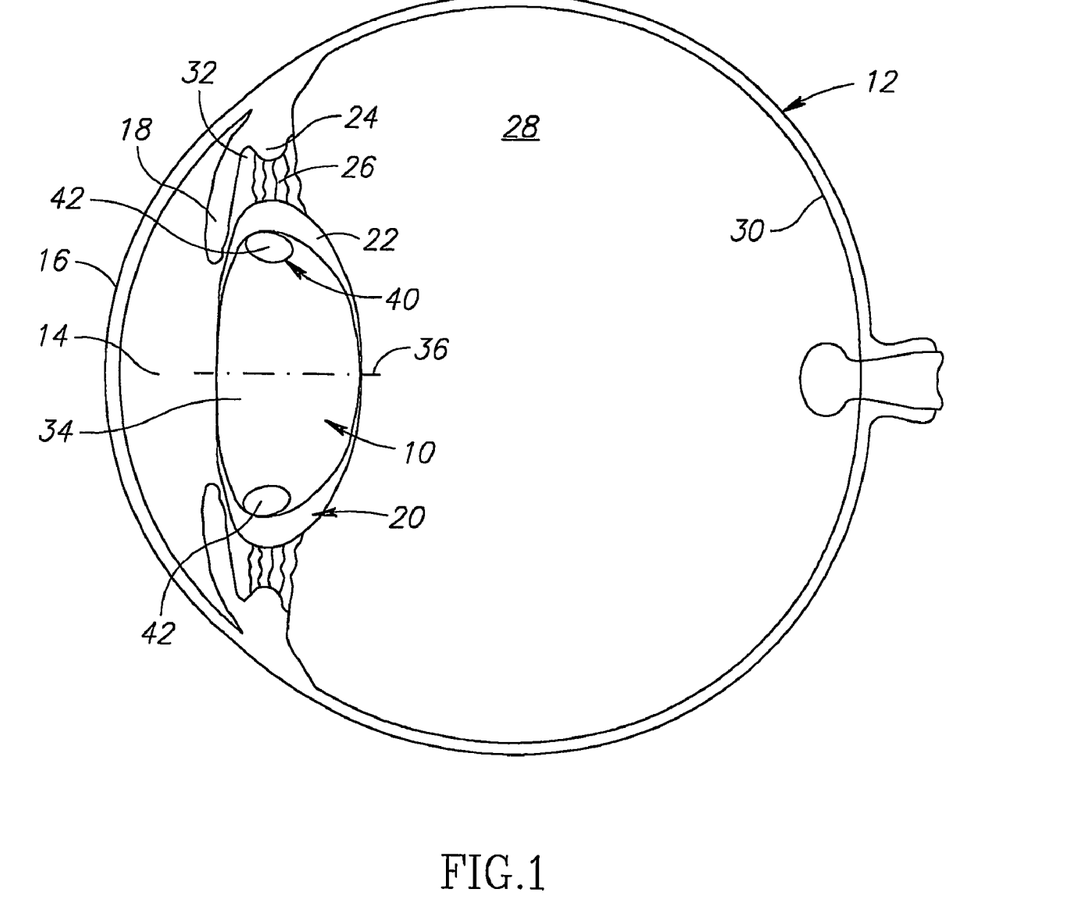
FIG. 1 is a simplified sectional illustration of an intraocular lens (IOL) assembly, constructed and operative in accordance with an embodiment of the present invention, inserted in a capsular bag of an eye and prior to expansion of a tensing element of the IOL assembly.

Reference is now made to FIG. 1, which illustrates an eye 12 that has an anterior chamber 14 between a cornea 16 and an iris 18, and a posterior chamber 20 behind the iris 18 containing a crystalline lens (not shown in FIG. 1), which has a lens capsule or capsular bag 22 attached about its periphery to ciliary muscles 24 by zonules 26. A vitreous chamber 28 is behind the capsular bag 22 containing vitreous humor, and a retina 30 is at the rear of the vitreous chamber 28. Between the iris 18 and ciliary muscles 24 is an annular crevice-like space called the ciliary sulcus 32.

FIG. 1 illustrates the eye 12 with the natural lens having been removed, such as by means of capsulorhexis (a form of anterior capsulotomy, such as continuous curvilinear capsulorhexis, for example) or a slit, and extraction of the cortex and nucleus of the lens, such as by means of phacoemulsification. An IOL assembly 10, constructed and operative in accordance with an embodiment of the present invention, is shown inserted in capsular bag 22. IOL assembly 10 may be inserted by any convenient means, such as by an introducer through a slit (not shown), as is well known in the art. The introducer may comprise a double-action tool that not only inserts IOL assembly 10, but may also be used to inflate a lens assembly of IOL assembly 10, as described hereinbelow.

IOL assembly 10 is preferably constructed of a clear, transparent, biologically compatible material, such as but not limited to, polymethylmethacrylate (PMMA), silicone, silicone rubber, collagen, hyaluronic acid (including the sodium, potassium and other salts thereof), hydrogel, such as acrylic or methacrylic hydrogels, e.g., hydroxyethyl methacrylate or methacrylic acid copolymer/partially hydrolyzed poly(2-hydroxyethyl methacrylate) (known as PolyHEMA), polysulfones, thermolabile materials and other relatively hard or relatively soft and flexible biologically inert optical materials, or any combination of such materials, such as a gel encapsulated in a polymer. IOL assembly 10 may thus be rigid, semi-rigid or foldable, for example.

IOL assembly 10 comprises a lens assembly 34, such as but not limited to, one or more monofocal or multi-focal lenses of any magnification, or optionally one or more lenses having a graded index of refraction, holographic (diffusing) lenses, doublet lenses which help prevent chromatic aberrations, Fresnel lenses, diffracting lenses, and/or telescopic lenses, for example.

As noted hereinabove, after removal of the natural lens, capsular bag 22 may become extended and zonules 26 may be slackened. In accordance with an embodiment of the present invention, IOL assembly 10 comprises a tensing element 40 for tensing ocular structure, such as zonules 26. Tensing element 40 may comprise a selectively inflatable and deflatable member 42 formed in a portion of lens assembly 34. Inflatable and deflatable member 42 may comprise one or more at least partially annular channels formed in the inner volume of lens assembly 34. The at least partially annular channel(s) may be generally concentric with a central axis 36 of lens assembly 34.

It is noted that throughout the specification and the claims the term "inflation" in all of its inflections encompasses not just inflation with a fluid (liquid or gas) but also any kind of expansion, such as thermal expansion. Similarly, the term "deflation" in all of its inflections encompasses not just deflation by expelling a fluid (liquid or gas) but also any kind of contraction, such as thermal contraction. Accordingly, the terms expansion and inflation are used interchangeably and the terms contraction and deflation are used interchangeably, and also encompass any mechanical, spring-like, chemical and biological structures.

Figure 2:
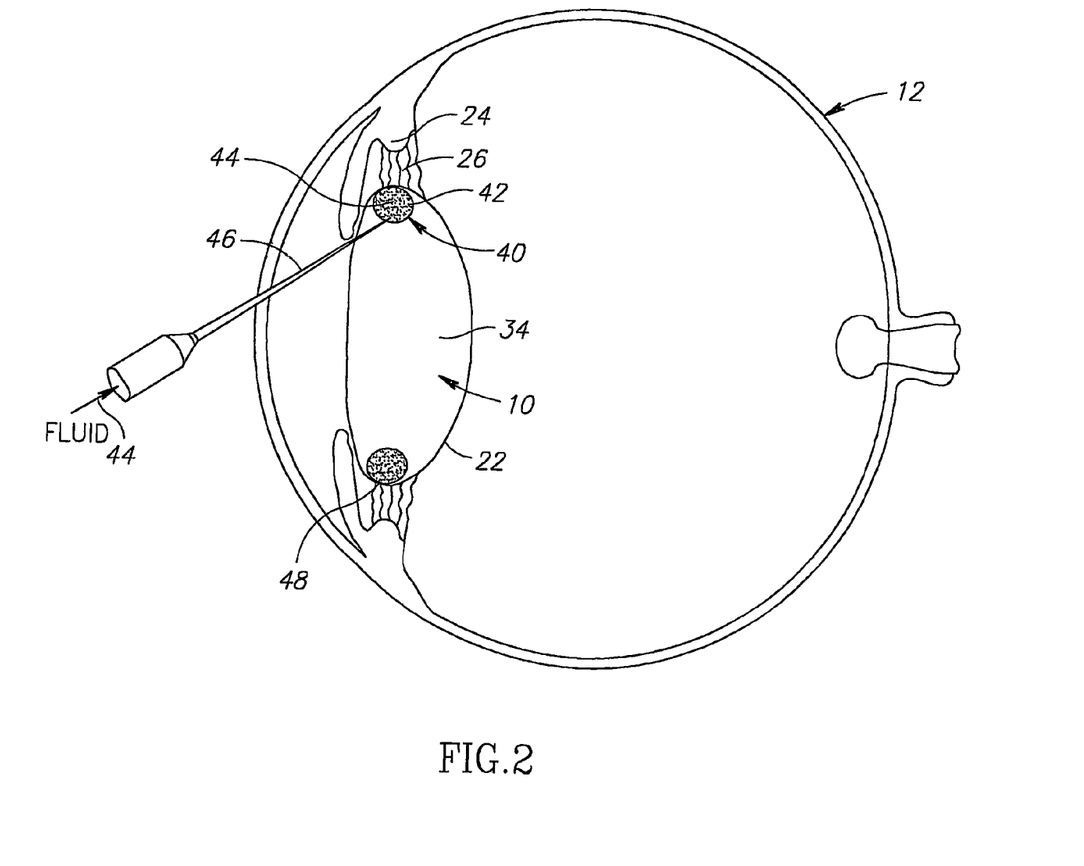
FIG. 2 is a simplified sectional illustration of expansion of the tensing element of the IOL assembly of FIG. 1, in accordance with an embodiment of the present invention.

Reference is now made to FIG. 2, which illustrates expansion of tensing element 40, in accordance with an embodiment of the present invention. Inflatable and deflatable member 42 may be inflated with a fluid 44 in a controlled manner and introduced by any convenient means, such as but not limited to, a needle 46 or a double-action introducer tool (not shown). Inflatable and deflatable member 42 may be equipped with a nipple (not shown) for facilitating introduction of fluid 44 therein. Fluid 44 may comprise any combination of one or more suitable biocompatible fluids, such as but not limited to, air, water, saline solution, vitreous humor and the like. Fluid 44 may be single phase (i.e., liquid phase alone or gaseous phase alone) or dual phase (i.e., a combination of liquid and gaseous phase). Inflation of inflatable and deflatable member 42 preferably causes lens assembly 34 to fill capsular bag 22, and may return capsular bag 22 to its original volume, shape or size. It is noted that zonules 26 are still slackened and not tensed.

As mentioned hereinabove, the vitreous humor may be used as the fluid 44 to inflate inflatable and deflatable member 42 in a controlled manner. In such an embodiment, the inflatable and deflatable member 42 may initially absorb the vitreous humor by osmosis through pores of the material of IOL assembly 10 into member 42, whereupon member 42 expands. With time, the osmotic pressure preferably changes such that the vitreous humor exits member 42 through the pores, thereby deflating member 42. Thus, in this manner, member 42 may be expanded and deflated in a controlled manner.

The expansion of inflatable and deflatable member 42 brings an interface element 48 of IOL assembly 10 into contact with the inside of capsular bag 22 in the region of the zonules 26. Interface element 48 may comprise a roughened perimeter of IOL assembly 10, protrusions, haptics, growth factor or biological adhesive, for example. The expanded IOL assembly 10 is retained in the expanded configuration until interface element 48 becomes fixed to the inside of capsular bag 22, such as by fibrosis or adhesion or bioadhesion.

Figure 3:
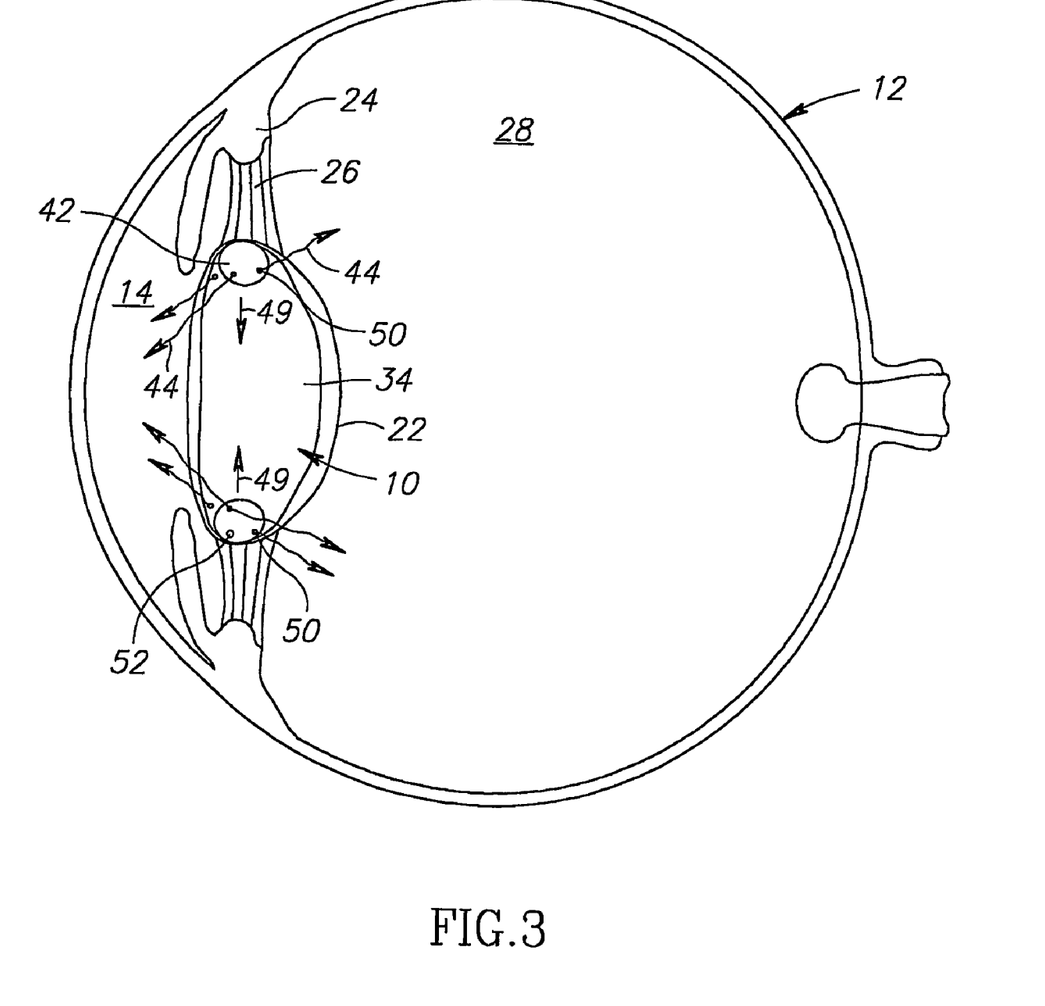
FIG. 3 is a simplified sectional illustration of the IOL assembly of FIG. 1 after attachment of the IOL to ocular structure and after contraction of the tensing element, which pulls the zonules into tension in accordance with an embodiment of the present invention.

Reference is now made to FIG. 3. After fixation of IOL assembly 10 to the inside of capsular bag 22, inflatable and deflatable member 42 may be deflated, which pulls zonules 26 into tension, generally in a direction towards the inner volume of lens assembly 34, as indicated by arrows 49. Inflatable and deflatable member 42 is thus a variably expansive member that selectively applies a tensing force on the ocular structure in a direction towards the inner volume of lens assembly 34, so as to tense the ocular structure.

Inflatable and deflatable member 42 may be deflated by any suitable means, such as but not limited to, fluid 44 exiting through one or more apertures 50 formed in inflatable and deflatable member 42. Apertures 50 may be purposely formed in member 42 or may comprise pores of a biologically compatible material used to make IOL assembly 10. Such an arrangement allows for fluid 44 to escape in a controlled manner. As another alternative, inflatable and deflatable member 42 may be simply punctured with a needle or laser (not shown). As yet another alternative, inflatable and deflatable member 42 may comprise a biodegradable plug 52 adapted to degrade with time and thereby cause deflation of member 42. The skilled artisan will appreciate that the invention is not limited to these examples and inflatable and deflatable member 42 may be deflated in any other suitable manner. Fluid 44 that exits inflatable and deflatable member 42 may drain to anterior chamber 14 or vitreous chamber 28, for example.

The tensing force created by the deflation of inflatable and deflatable member 42, which tenses zonules 26, tends to restore the natural accommodation capability of the eye 12, and enables the ciliary muscles 24 and zonules 26 to control the optical power of the lens assembly 34 as in the normal operation of a young, healthy eye. Lens assembly 34 may change its convexity or any other geometric parameter of its shape, when changing its optical power during accommodation, as in the normal operation of a young, healthy eye. IOL assembly 10 has good contact with capsular bag 22 at the junction of the zonules 26, and may provide uniform tension on zonules 26 and uniform forces on capsular bag 22. IOL assembly 10, by being selectively expandable and contractible, adapts and adjusts itself to any eyeball size.

Figure 4:
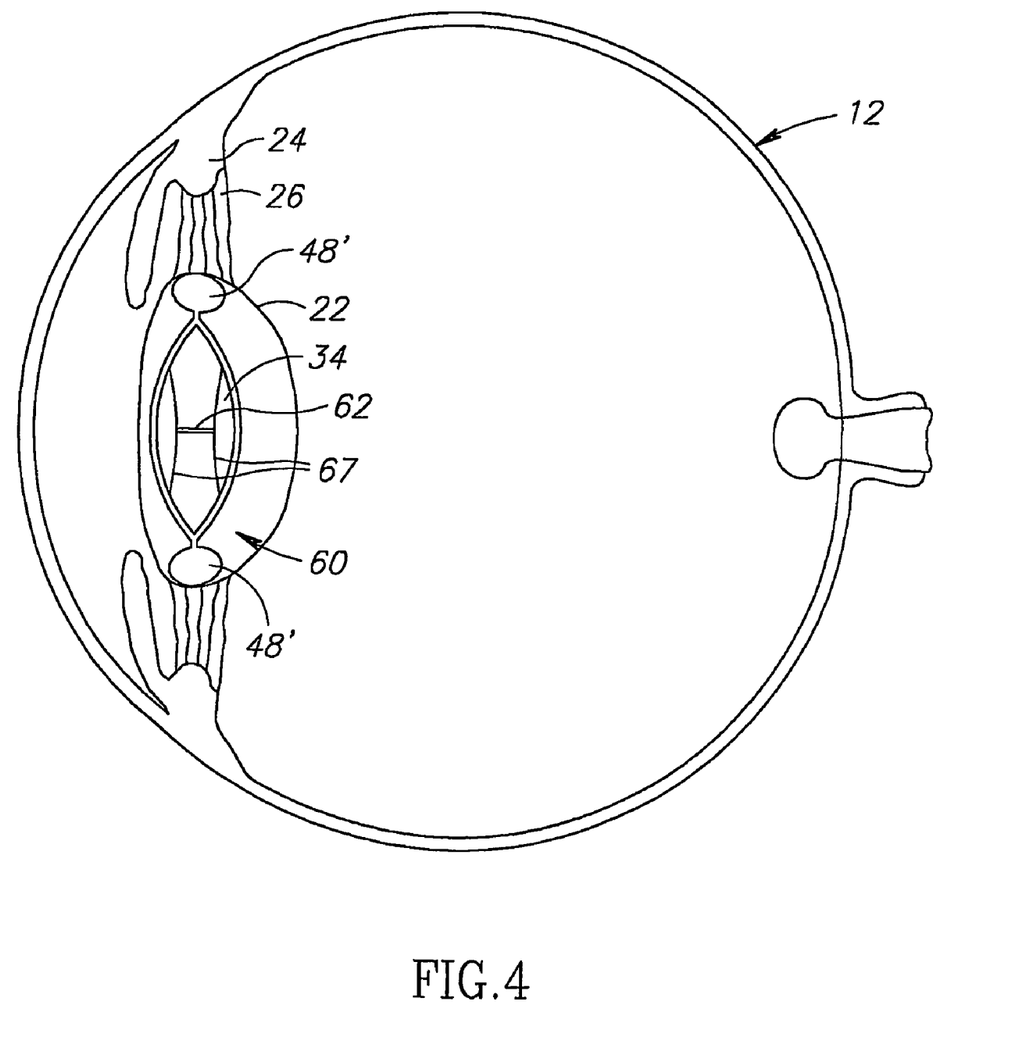
FIG. 4 is a simplified sectional illustration of an IOL assembly, constructed and operative in accordance with another embodiment of the present invention, which comprises a variably expansive member in a first configuration wherein there is generally no application of a tensing force on ocular structure.

Reference is now made to FIG. 4, which illustrates a variation of IOL assembly 10, designated IOL assembly 60, constructed and operative in accordance with another embodiment of the present invention. Elements common to both IOL assembly 10 and IOL assembly 60 are designated by like numerals. In IOL assembly 60, the tensing element comprises a variably expansive member 62, which in a first configuration does not generally apply a tensing force on the ocular structure, but which in a second configuration does apply a tensing force on the ocular structure, as is now described.

FIG. 4 illustrates IOL assembly 60 inserted in capsular bag 22. The variably expansive member 62 may comprise a suture, rod, beam or other structural member, that extends from one portion of lens assembly 34 to another portion of lens assembly 34, such as but not limited to, opposing internal surfaces of lens assembly 34, e.g., anterior and posterior faces or lenses 67 of the assembly. As long as the variably expansive member 62 is attached to both portions of lens assembly 34, variably expansive member 62 applies a preload to lens assembly 34 that pushes the perimeter of lens assembly 34 towards the ocular structure (e.g., zonules 26). The zonules 26 are still slackened and not tensed. The preload brings an interface element 48' of IOL assembly 60 into contact with the inside of capsular bag 22 in the region of the zonules 26. The expanded IOL assembly 60 is retained in the expanded configuration until interface element 48' becomes fixed to capsular bag 22, such as by fibrosis or adhesion.

Figure 5:
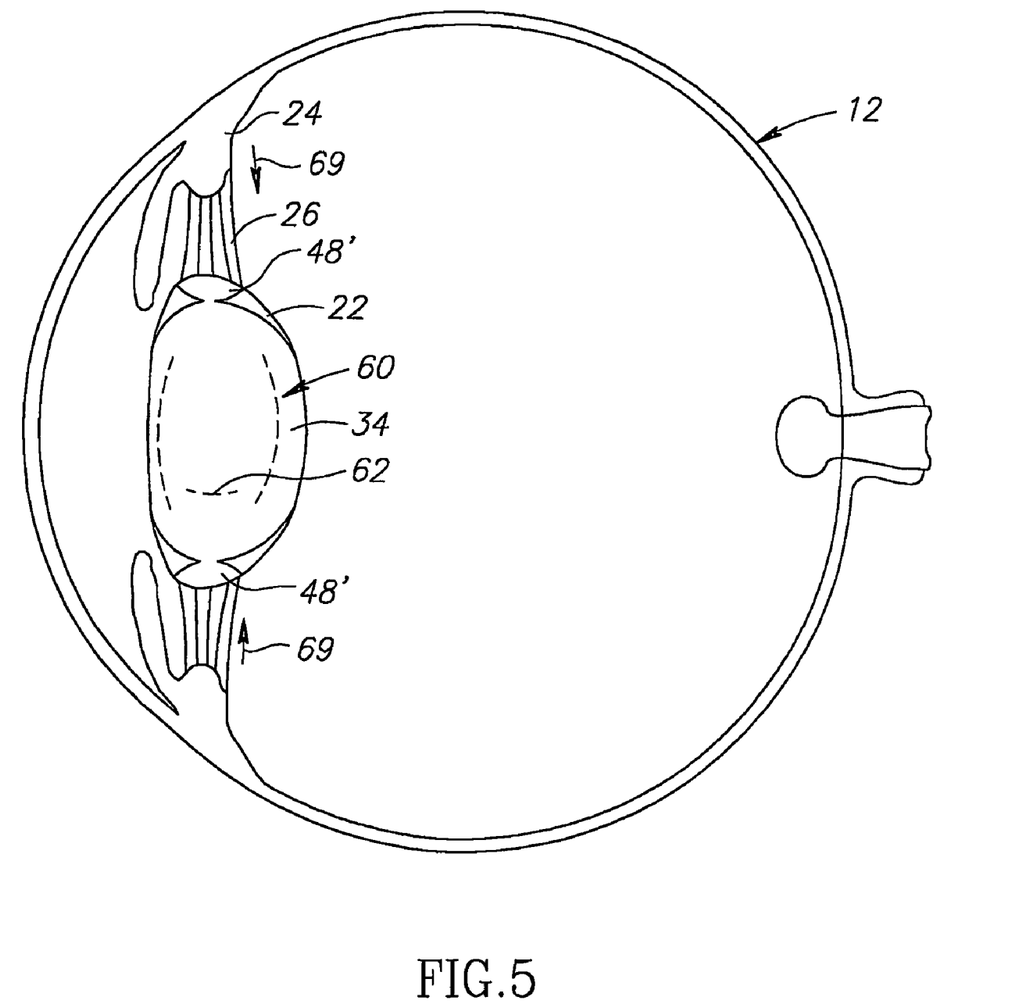
FIG. 5 is a simplified sectional illustration of the IOL assembly of FIG. 4, with the variably expansive member in a second configuration wherein a tensing force is applied on the ocular structure, in accordance with an embodiment of the present invention.
Figure 6:
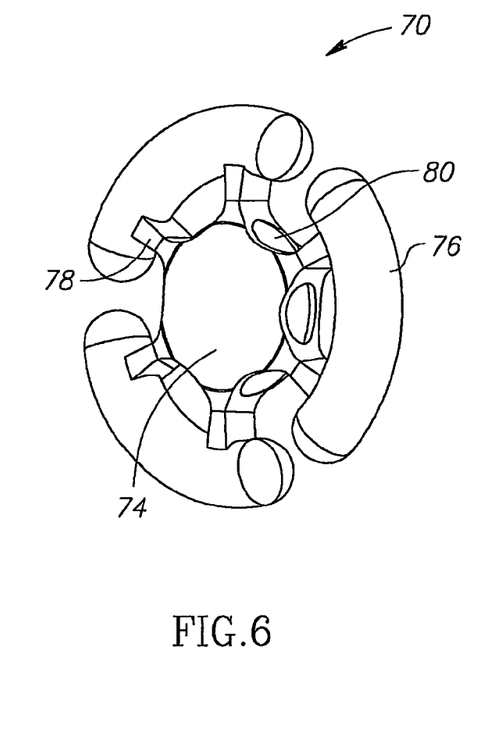
FIGS. 6, 7 and 8 are simplified pictorial, front-view and sectional illustrations, respectively, of an intraocular lens (IOL) assembly, constructed and operative in accordance with yet another embodiment of the present invention.
Figure 7:
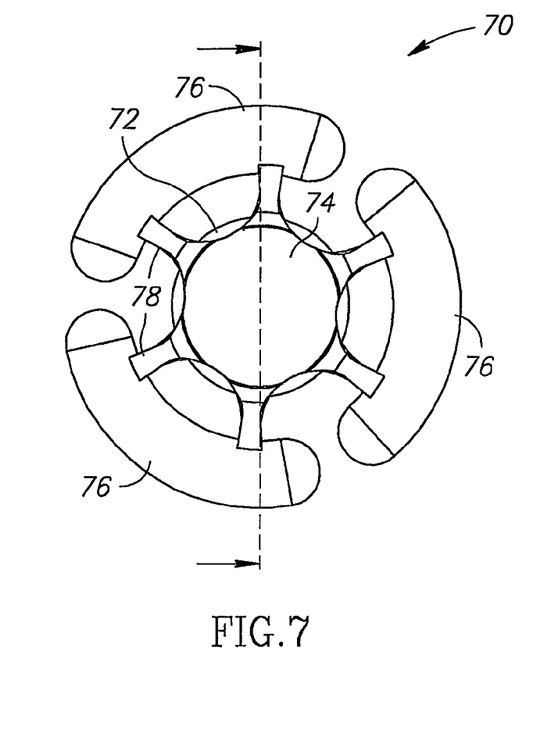
Figure 8:
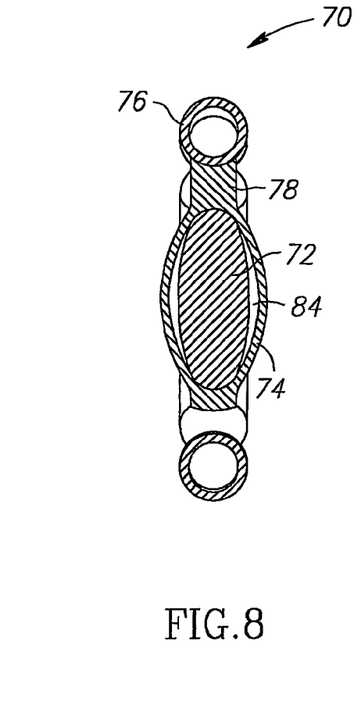
Figure 9:
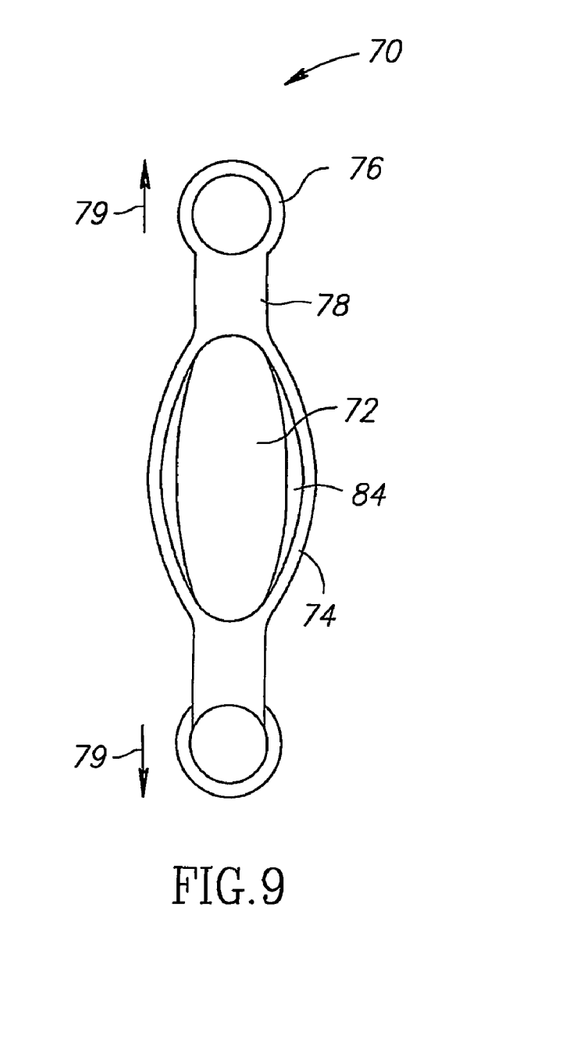
FIGS. 9, 10 and 11 are simplified side-view illustrations of expansion, contraction and accommodative movement, respectively, of the IOL assembly of FIGS. 6-8, in accordance with an embodiment of the present invention.
Figure 10:
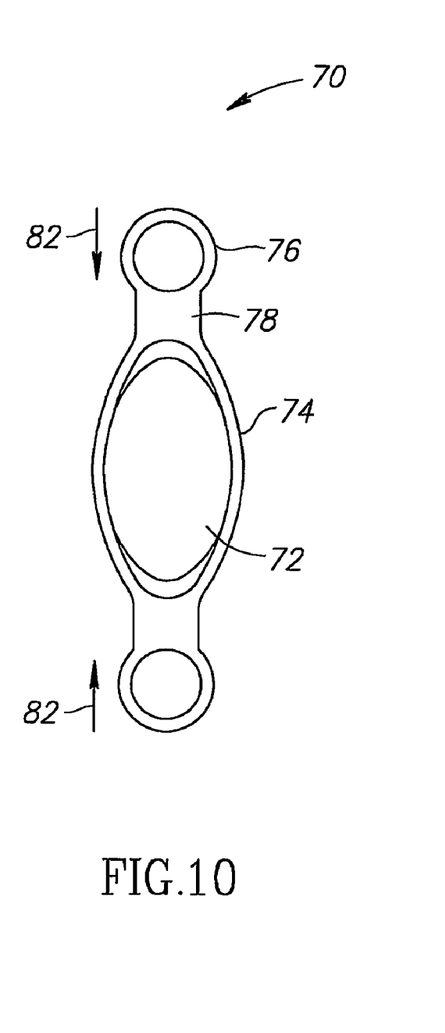

Reference is now made to FIG. 5. After fixation of IOL assembly 60 to the inside of capsular bag 22 in the region of the zonules 26, the connection of variably expansive member 62 to one or more of the portions of lens assembly 34 may be severed, dissolve or otherwise removed or destroyed (such as by laser cutting, knife incision, or being made of biodegradable materials which degrade and dissolve with time, and the like) which pulls zonules 26 into tension, generally in a direction towards the inner volume of lens assembly 34, as indicated by arrows 69. The variably expansive member 62 thus applies a tensing force on the ocular structure in a direction towards the inner volume of lens assembly 34, so as to tense the ocular structure.

Reference is now made to FIGS. 6-11, which illustrate an intraocular lens (IOL) assembly 70, constructed and operative in accordance with yet another embodiment of the present invention. IOL assembly 70 may comprise an optic (i.e., lens assembly) 72, such as but not limited to, a convex lens, concave lens, holographic lens, diffractive lens, or any other kind of lens, with or without any kind of coating, disposed in an inflatable and deflatable member 74. Inflatable and deflatable member 74 may comprise inflatable and deflatable haptics 76, such as but not limited to, annular segments (partial rings) that are attached to inflatable and deflatable member 74 by means of struts 78. Inflatable and deflatable member 74 may be provided with apertures 80 through which a periphery of optic 72 passes, in order to accommodate, control or define the movement of inflatable and deflatable member 74 during expansion and contraction.

Haptics 76 may be inflated with a fluid as described similarly hereinabove for the embodiment of FIG. 2, in a controlled manner and introduced by any convenient means, such as but not limited to, a needle or a double-action introducer tool (not shown). The fluid may comprise any combination of one or more suitable biocompatible fluids, such as but not limited to, air, water, saline solution, vitreous humor and the like. The expansion of haptics 76 (in the direction of arrows 79, FIG. 9) brings them into contact with the inside of the capsular bag (not shown in FIG. 9) in the region of the zonules (not shown in FIG. 9). Haptics 76 serve as interface elements to the inside of the capsular bag. Haptics 76 may comprise a roughened surface, protrusions, growth factor or biological adhesive, for example. The expanded IOL assembly 70 is retained in the expanded configuration until haptics 76 become fixed to the inside of the capsular bag, such as by fibrosis or adhesion or bioadhesion.

Figure 11:
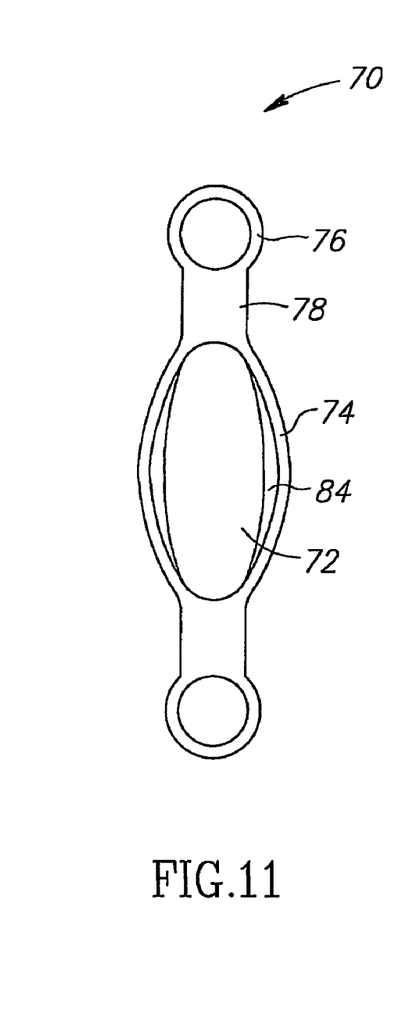

After fixation of IOL assembly 70 to the inside of the capsular bag, haptics 76 of inflatable and deflatable member 74 may be deflated (FIG. 10), which pulls the zonules into tension, generally in a direction towards the inner volume of IOL assembly 70, as indicated by arrows 82. Afterwards, natural accommodation of the eye, which may involve tensing and relaxing of the zonules, causes corresponding changes in the shape of IOL assembly 70, as seen in FIG. 11. Inflatable and deflatable member 74 is thus a variably expansive member that selectively applies a tensing force on the ocular structure in a direction towards the inner volume of IOL assembly 70, so as to tense the ocular structure. Inflatable and deflatable member 74 may be deflated by any suitable means, as described similarly hereinabove for the embodiment of FIG. 2. The spaces between the anterior and posterior faces of inflatable and deflatable member 74 and optic 72 may be filled with a fluid 84, such as but not limited to, water, saline solution, vitreous humor and the like. The optic 72 may comprise a lens with a predefined shape, as mentioned before, within a predefined range of diopters. Different optics, of course, may be provided to cover a range of diopters. The optical combination of inflatable and deflatable member 74, optic 72 and fluid 84 may provide enhanced optical magnification and/or refraction properties. IOL assembly 70 thus has more than three optical surfaces: the outer and inner anterior and posterior faces of inflatable and deflatable member 74 and the anterior and posterior faces of optic 72 (a total of six optical surfaces).

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An intraocular lens assembly comprising:
   a lens assembly comprising an interface element adapted for attachment to an ocular structure, said lens assembly comprising a tensing element adapted to expand and contract relative to said lens assembly and apply a tensing force on said ocular structure directed towards an inner volume of said lens assembly;
   wherein said tensing element comprises a selectively inflatable and deflatable member, said selectively inflatable and deflatable member being inflatable with a fluid, and wherein said selectively inflatable and deflatable member is adapted to absorb and expel said fluid by osmotic pressure, and wherein said interface element comprises at least one inflatable and deflatable haptic.

2. The intraocular lens assembly according to claim 1, wherein said selectively inflatable and deflatable member comprises at least one at least partially annular channel formed in the inner volume of said lens assembly.

3. The intraocular lens assembly according to claim 2, wherein said at least one at least partially annular channel is generally concentric with a central axis of said lens assembly.

4. The intraocular lens assembly according to claim 1, wherein said selectively inflatable and deflatable member is inflated with a fluid, and wherein said selectively inflatable and deflatable member is formed with apertures trough which said fluid flows.

5. The intraocular lens assembly according to claim 1, wherein said at least one inflatable and deflatable haptic comprises an annular segment attached to said selectively inflatable and deflatable member by means of a strut.

6. The intraocular lens assembly according to claim 1, wherein spaces between anterior and posterior faces of said selectively inflatable and deflatable member and said lens assembly are filled with a fluid.

7. The intraocular lens assembly according to claim 1, wherein said lens assembly comprises at least one of a convex lens, a concave lens, a monofocal lens, a multi-focal lens, a lens having a graded index of refraction, a holographic lens, a doublet lens, a Fresnel lens, a diffracting lens, and a telescopic lens.

8. The intraocular lens assembly according to claim 1, wherein said lens assembly comprises a lens with a predefined shape within a predefined range of diopters.

* * * * *